United States Patent [19]
Weber et al.

[11] Patent Number: 5,172,514
[45] Date of Patent: Dec. 22, 1992

[54] INSECT TRAP

[75] Inventors: Terry Weber, Sunnyvale; Ramon Georgis, San Jose; Paul Pruitt, Half Moon Bay; Jean Wren, Palo Alto, all of Calif.

[73] Assignee: Biosys Corporation, Palo Alto, Calif.

[21] Appl. No.: 615,609

[22] Filed: Nov. 19, 1990

[51] Int. Cl.$^5$ .............................................. A01M 1/20
[52] U.S. Cl. .................................... 43/132.1; 43/124
[58] Field of Search ..................... 43/124, 132.1, 131

[56] References Cited

U.S. PATENT DOCUMENTS
4,320,130  3/1982  Balsley et al. .

FOREIGN PATENT DOCUMENTS
2174907  10/1988  United Kingdom .

OTHER PUBLICATIONS
Zukoswski et al., *Roczniki Panstwowego Zakladu Higieny* (1984) 35:451–457.
Boush, G. M., University of Wisconsin, Madison, Wis., *Reports of Results of Government Contracts* 18326 (1983).
Boush, G. M., University of Madison, Wisconsin, WI, *Reports of Results of Government Contracts* 18226 (1982).
Boush, G. M., University of Wisconsin, Madison, WI, *Reports of Results of Government Contracts* 18206 (1981).
Skierska et al., *Bull Inst Maritime Trop Med* (1976) 27:207–227.
Zervos et al., *Can J Zol* (1989) 67:1609–1611.

*Primary Examiner*—Kurt C. Rowan
*Attorney, Agent, or Firm*—Morrison & Foerster

[57] ABSTRACT

Traps which include nematode infective juveniles as a toxic agent are effective in decreasing insect populations in a variety of environments. The traps of the invention contain a stable infective juvenile nematode population in a configuration which encourages nictation and the traps provide an effective harborage for the roaches or other insects. Relative humidity is maintained in the traps by the supply of molecular water.

18 Claims, 3 Drawing Sheets

INSECT TRAP

TECHNICAL FIELD

The invention is directed to an apparatus which provides effective means to control insects, especially cockroaches, in an environment by use of entomogenous nematodes as the toxic agents More specifically, the invention concerns insect traps that behave as attractants and do not pose a danger to nontargeted species in the environment.

BACKGROUND ART

It has for some time been established that infective juveniles of the order Rhabditida, especially those of the genera Steinernema and Heterorhabditida are able to effect killing of the German cockroach *Blatella germanica* as well as other insects. In tests using direct application of the nematodes to subject cockroaches with a small sponge soaked in nematodes or a petri dish lined with filter paper containing the nematodes, high levels of mortality were obtained in cockroaches using infective juveniles from these genera, especially the species *Steinernema feltiae* previously known as *Neoaplactana carpocapsae*. A number of groups have reported these results. See, for example, Locatelli, D. P. et al., *La Difesa delle Piante* (1987) 10:339-348; Zukowski, K., *Roczniki Panstwowego Zakladu Higieny* (1984) 35:451-457; Boush, G. M., University of Wisconsin, Madison, Wis., *Reports of Results of Government Contracts*, 18326 (1983); 18226 (1982); 18206 (1981); and Skierska, B. et al., *Bull Inst Maritime Trop Med* (1976) 27:207-227. The ability of *H. heliothidis* to kill the American species *Periplaneta americana* has also been confirmed by Zervos, S. et al , *Can J Zool* (1989) 67:1609-1611.

However, mere knowledge that certain species of entomogenous nematodes can successfully kill insects when the infective juveniles are directly introduced to them does not permit successful design of traps which will capitalize on this ability of the nematodes in a practical environment. Advantage must be taken of the behavior of the target insect so that the insect is brought into proximity with the infective juveniles (IJs) and the IJs themselves must be maintained in a condition to effect the infestation of the insects. The design of a successful roach trap, fly trap, yellow jacket trap, or trap for other insects therefore, requires an understanding of the behavior of both the target insect and the infectious agent, as well as a plan for construction which takes advantage of these characteristics.

The need for providing a response to at least some of these parameters in an analogous context is recognized in British patent GB 2,174,907, granted 19 Oct. 1988. In the apparatus described, which is designed specifically for flying insects, live entomophilic nematodes are maintained on a moist absorbent pad which is kept from desiccating by a supply of liquid water either directly added to the pad through an external source or conducted into the pad by capillary action from a reservoir of liquid water with which the pad is in contact. The description further indicates that an attractant for the insect, such as a pheromone, must be included in order to provide incentive for the flying insects to contact the pad containing the nematodes. All of the designs are open to the atmosphere, as the aim is to attract flying insects specifically. Although it is mentioned in the description that these apparatuses may be used to control cockroaches, it is clear that the designs presented are not appropriate to do so since they would require the cockroach to surmount vertical surfaces—a behavior not attractive to these insects. The described apparatuses have other disadvantages as well—as the nematodes are evenly distributed throughout the absorbent pad, and as the pad is kept saturated with liquid water, the nematodes do not exhibit nictation behavior, and approximately 70% of them escape from the trap within a day. Furthermore, practical quantities of liquid water can keep the absorbent pad moist for only 3-7 days without adding more water to the reservoir.

It would be useful to provide a device to control roaches and other insects in an environment which could be left in place for substantial periods of time, which does not, in the case of roaches at least, require expensive attractants or bait and which does not pose a hazard to unintended targets. The present invention provides such a device.

DISCLOSURE OF THE INVENTION

The invention provides means to control insects, and, in particular, cockroaches in homes, factories, farms, restaurants, and other locations where these insects are a problem. The invention apparatus relies on the environmentally safe mechanism of utilization of entomogenous nematodes to effect destruction of the insect population, and does not require messy or expensive bait to attract the insects to the traps. The traps of the invention can be maintained for substantial periods of time in location, and can be made in disposable form or can be resupplied with the infective juveniles.

Accordingly, in one aspect, the invention is directed to an apparatus for decreasing the population of insects in an environment, wherein the apparatus comprises an enclosure which includes a means for entry by the insect. Inside of the enclosure is a source of live and active entomogenous infective juvenile nematodes which are maintained in an environment which allows them to migrate to a surface area acceptable to the insects. The construction of the nematode source is such that nictation behavior is effected in the nematodes at the surface—i e., the worms "stand up" and wiggle, as described below The nematode source is kept moist by maintaining the relative humidity in the enclosure at 95% RH or greater by introducing only molecular water into the enclosure.

In another aspect, the invention is directed to a method to decrease the population of insects in an environment by use of the invention apparatus.

In still another aspect, the invention is directed to a method to effect the slow release of a nictating nematode population which method comprises maintaining infective juveniles in a gel, wherein the viscosity of the gel is reduced by the shear forces of the infective juveniles and/or increased relative humidity, and wherein the gel is of sufficient volume to delay the appearance on the surface of the gel of the infective juveniles originating at the interior of the gel. In still another aspect, the invention is directed to this slow release composition.

MODES OF CARRYING OUT THE INVENTION

Figure 1:
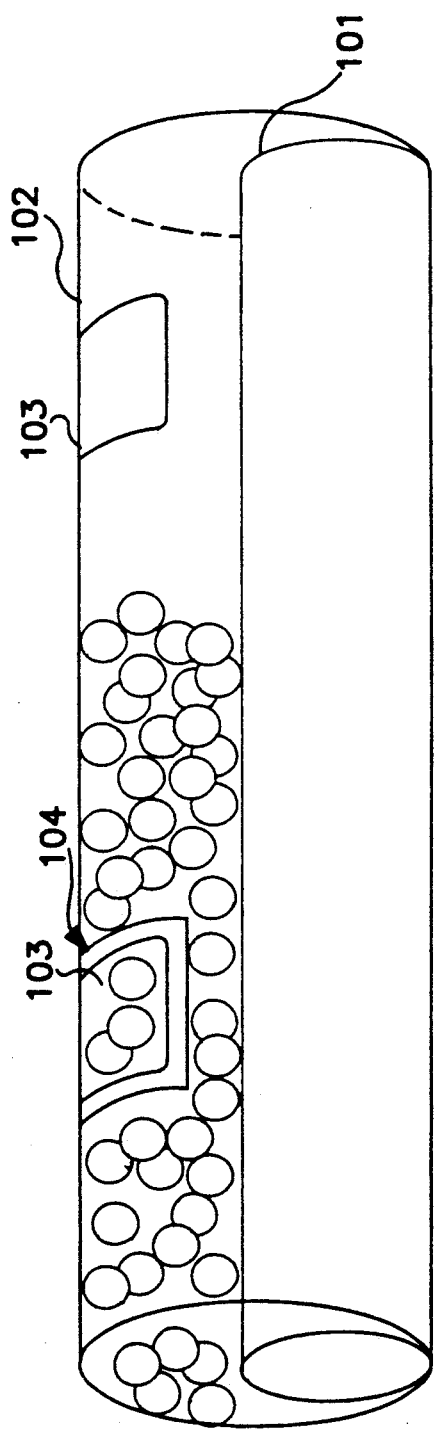
FIG. 1 shows a diagram of an embodiment of the apparatus of the invention which employs a multilayered paper tube as a means for nematode release.

Infective juveniles of some genera of nematodes, specifically the Steinernema and Heterorhabditida, are known to be effective in killing insects, including the German cockroach B. germanica. The infective juveniles of these genera are obtainable from culture media. They form normally under conditions of "hardship" which occur in such culture media in which large and dense populations of the nematodes are raised.

Nematodes in general exhibit a life cycle in which sexual reproduction of the adults results in embryos which molt through several larval stages before maturing into adults and renewing the cycle. At the third larval stage, the nematodes can progress through subsequent changes to maturity directly, or can be diverted to a modified form referred to herein as the "infective juvenile" stage. In this form, the nematode is ensheathed in an extra cuticle and requires only moisture and oxygen to survive. The infective juveniles have no other nutritional requirements. The infective juvenile form is obtained under conditions where nutrients are in short supply, such as in an insect cadaver or in mass culture where the large population of the nematodes depletes the food supply.

In the infective juvenile stage, the nematodes are capable of infecting insects by entering a body opening where the more favorable environment permits sufficient dissolution of the cuticle to permit exit of the larvae and release of a symbiotic bacterium which inhabits the nematodes. In general, this has the effect of permitting the nematode to resume its life cycle on its pathway to becoming an adult, and the symbiont releases toxins which result in the death of the insect.

In the cockroach and other insects, including flies and yellow jackets, entry of the infective juveniles into the interior or hemocoel of the insect is most efficiently conducted through the spiracles, which are the breathing tubes distributed along the abdomen, or through the anus. Ingestion through the mouth is substantially less efficient; in the roach approximately 200 nematode infective juveniles ingested by mouth have an equivalent effect to only one ingested by these alternate routes. Since the introduction of the worms, therefore, is passive with respect to the insect, and active with respective to the IJ, the IJ must be supplied in a manner which permits this activity. Accordingly, the devices of the invention are designed so as to encourage "nictation" behavior by the IJs. In this behavior, the IJs, which appear as thin rods approximately 0.4 mm in length, balance one end on a surface on which they are disposed and "wave" the distance of their length. Nictation behavior is encouraged on relatively dry surfaces; nictation does not occur when the surface is covered with liquid.

The apparatus of the invention is thus provided with a substantial number of nematodes in an infective juvenile stage which are maintained in a form which will permit their slow release onto a surface at which nictation behavior will be exhibited. A particularly advantageous mechanism for this release is from a slow-release gel as further described hereinbelow.

In addition to providing means to accommodate the behavior patterns of the IJs, the apparatus of the invention must accommodate the behavior patterns of the target insect. With respect to the cockroach, previous traps have utilized baits or other attractants; the apparatus of the invention relies simply on the attraction of roaches to moisture and to their tendency to harbor in closed spaces. It has been found that the effectiveness of the traps can be greatly increased by providing an enclosure and that the high humidity environment provided by the release of molecular water is sufficient to attract the cockroaches even when alternative attractants (such as food) are provided in a test environment. The roach traps of the invention are therefore designed to provide an enclosed space in which the roaches can harbor in the proximity of the nematodes, and a high humidity, but not liquid water, environment to attract them. The level of light should also be reduced.

Traps designed to eliminate the population of other insects must, of course, be designed differently to accommodate the behavior patterns of their respective targets. For example, traps designed to attract flying insects such as flies and yellow jackets should have an enlarged enclosure, can admit light, and most frequently do require the disposition of food, bait, or other attractants in the trap. A particularly favored form of attractant is a pheromone appropriate to the target insect.

Most of the traps of the invention require the maintenance of relative humidity inside the trap of 95% or more. This is accomplished by the release of molecular water, either by providing a source of liquid water separated from the enclosure by a suitable membrane, or by providing a source of molecular water as a gel.

THE NEMATODE SUPPLY

An essential feature of the apparatus of the invention is a means to supply infective juveniles which exhibit nictation behavior over a long time period of several days to several weeks. In order to provide this supply, a source of live and active entomogenous juvenile nematodes must be provided in contact with a surface which will accommodate and effect the nictation behavior of the IJs. In general, the supply portion of the nematode source is kept moist and the surface of the source relatively dry—at least free of liquid water.

A particularly effective arrangement utilizes a gel which serves as a slow-release mechanism for IJs. The gel is typically hygroscopic and releases the nematodes as water is gathered into the gel. The semisolid hydrogel can be prepared from conventional gums and components and "set" in the presence of the nematode preparation. In general, the slow-release gel is obtained by first preparing a slurry of the gelling ingredients such as carrageenan, tragacanth, collagen, and the like; then mixing the gel with a slurry of nematodes preferably at about 100,000–800,000 IJs/ml. The gel is then set by the addition of a suitable polyvalent ion, preferably after soaking the slurry into a portion of a porous carrier such as sponge or paper.

In general, the nematode infective juveniles are obtained using a mass culture method to provide the requisite number of organisms. A number of mass culture methods have been described in the art: for example, Bedding, R. A., *Ann App Biol* (1984) 104:117–120, provides such a method which uses a solid phase matrix of plastic foam impregnated with homogenized animal tissue; Dutky, S. R., et al., *J Nematol* (1967) 13:140, describe an agar-based culture; Wouts, W. M., et al., *J Nematol* (1981) 13:467–469, describe a medium which is set on a solid support or foam. Liquid cultures are considered more efficient; PCT application W086/01074, published 27 Feb. 1986, describes stirred reactor methods for monoxenic cultures of nematodes. PCT publication W089/04602, published 1 Jun. 1989, describes improved media for mass production of infective juveniles in liquid culture.

The infective juveniles obtained using the above-referenced methods are harvested by filtration or centrifugation or other standard harvest means and can be used directly in slurries with the gelling ingredients. As illustrated in the table below, the gelling components such as carrageenan and locust bean gum are first mixed with the nematode slurry to obtain a viscous liquid; the setting agent is then added with or without the prior application of heat, and with or without the viscous liquid being distributed through a portion of a reticulated porous solid support. When gelled without the use of the porous support, the resulting gel forms a continuum, analogous to standard gelatin used in foodstuffs. Typical combinations of ingredients for the slow-release gels are as follows:

volume to require time for the IJs contained at the interior of the gel, or at the bottom of the gel if the gel is disposed on an impervious surface, to reach the top of the gel surface. In general, the volume is adequate if about 5 grams of gel are spread over a 20 $cm^2$ surface. The gel should be treated with an antimicrobial agent to prevent spoilage.

For use in the insect traps of the invention, however, the gel must be provided with a surface which remains relatively dry; roaches will not walk over a liquid surface and the infective juveniles will not nictate on a liquid surface. Furthermore, the surface must provide adequate surface area to prevent escape of the infective juveniles into the surroundings. Several approaches can be used. Particles can be distributed over the surface to provide the required surface area. These particles may be of any composition as long as they are nontoxic to the nematodes and provide a rough surface. Foam particles—for example, polyurethane foam, polystyrene foam, or any other biocompatible foam—can be used. Cellulose, sand, ground coral, apatite, or other available particulate could also be used. Preferably, the gel is set within a portion of a volume of a porous solid support block, which block can be composed of sponge, polyurethane or polystyrene foam, or even cardboard. The gel is slurried into the block so that a thin surface remains unwetted. The gel is then set in the slurried portion leaving a surface which provides the required surface area and rough texture.

TABLE 1

| Gelling Components | | Setting Agent |
|---|---|---|
| 1) Carrageenan:Locust Bean Gum (Superior) | 3:1 | 0.2M $CaCl_2$ |
| 2)* Carrageenan:Locust Bean Gum (Superior) | 3:2 | 0.2M $CaCl_2$ |
| 3) Carrageenan:Locust Bean Gum (Superior) | 6:1 | 1M $K_2HPO_4$ |
| 4) Carrageenan:Locust Bean Gum (Superior) | 3:1 | 0.5M $K_2PO_4$ |
| 5)* Carrageenan:Locust Bean Gum (Superior) | 6:1 | 0.5M $CaCl_2$ |
| 6)* Carrageenan:Locust Bean Gum (Extra) | 6:2 | 0.2M $K_2HPO_4$ |
| 7) Carrageenan:Locust Bean Gum (Extra) | 3:2 | 1M, 0.5M $CaCl_2$ |
| 8) Carrageenan:Locust Bean Gum (Extra) | 3:1 | 1M $CaCl_2$ |
| 9) Carrageenan:Locust Bean Gum (Extra) | 6:1 | 0.5M $CaCl_2$ |
| 10)* Carrageenan:Locust Bean Gum (Extra) | 6:1 | 1M, 0.5M $K_2HPO_4$ |
| 11)* Carrageenan:Locust Bean Gum (D200) | 3:2 | 0.5M $CaCl_2$ |
| 12) Carrageenan:Locust Bean Gum (D200) | 6:1 | 1M $K_2HPO_4$ |
| 13)* Carrageenan:Locust Bean Gum (D200) | 6:1 | 0.5M $K_2HPO_4$ |
| 14)* Carrageenan:Locust Bean Gum (Botanical) | 3:2 | 0.5M $CaCl_2$ |
| 15) Carrageenan:Locust Bean Gum (Botanical) | 6:1 | 0.5m $K_2HPO_4$ |
| 16) 3 Stamere NI | | 1M, 0.5M $CaCl_2$<br>1M, 0.5M $K_2HPO_4$ |
| 17) 6 Stamere NI | | 1M $CaCl_4$ |
| 18) Tic tragacanth:Ticxan | 3:1 | 0.5M, 1M $K_2HPO_4$<br>1M $CaCl_2$ |
| 19) Tic tragacanth:Ticxan | 6:1 | 1M $K_2HPO_4$ |
| 21) Carrageenan:Locust Bean Gum (Superior) | 3:1 | 0.2M $CaCl_2$ |
| 20) Tic tragacanth:Locust Bean Gum (Superior) | 3:1 | 0.5M $K_2HPO_4$<br>0.2M $NaBO_2$ |
| 21)* Tic tragacanth:Locust Bean Gum (Superior) | 3:1 | 0.2M, 0.5M $NaBO_2$ |
| 22) Tic tragacanth:Locust Bean Gum (Superior) | 6:1 | 0.2M $NaBO_2$ |
| 23)* Tic tragacanth:Locust Bean Gum (Superior) | 6:1 | 0.5M 1M $K_2HPO_4$ |
| 24) Tic tragacanth:Guar PF20 | 3:1 | 0.5M, 0.2M $NaBO_2$ |
| 25)* Locust Bean Gum D200:Ticxan | 3:0.4 | 0.5M $NaBO_2$ |
| 26) 2.4 Guar PF20 or Food | | 0.2M or 0.1M $NaBO_2$ |
| 27) 5 Guar Food | | 0.5M $NaBO_2$ |
| 28) CSW-2:Locust Bean Gum (Extra) | 3:1 | 0.2M KCl |

* - Heat before set

The combinations in Table 1 are merely illustrative; a large variety of gel ingredients can be used. The requirements of the gels are simply that the set gel be sufficiently hygroscopic so that the viscosity of the gel is lessened as the gel absorbs moisture from maintenance of a high relative humidity or that the gel is sufficiently thixatropic that the shear forces created by the IJs contained in it lower the viscosity so that the IJs can move through the gel.

The gel, then, whether impregnated into a porous support or not, becomes a slow-release mechanism for the IJs which it contains, provided that it is of sufficient

MAINTENANCE OF HUMIDITY

A source of molecular water is required to provide moisture to maintain an RH of 95% or more. As described in the section below directed to traps for which specific designs are provided, this source may be liquid water separated from the enclosure by a membrane which passes only water vapor. Alternatively, however, the enclosure can include, at a location distal to the nematode source, a water-liberating gel, such as swelled polyacrylamide, which provides water vapor. This gel can be affixed to a surface within the enclosure.

TRAP CONFIGURATIONS

The design of the particular trap will depend on the nature of the insect being targeted, as was stated above. For a trap designed to attract yellow jackets or flies, the openings in the enclosure are enhanced to permit ready entry of the insects. It is not harmful to permit light at comparable levels to ambience to exist in the trap. However, it is highly desirable in the case of these insects to provide a suitable attractant such as food, bait, or other attractants such as pheromone. These attractants should be disposed in a manner to provide encouragement for the insect to remain at the location at which nictation behavior is effected in the IJs. Thus, the attractant should be applied directly to the rough surface described above, or to an area adjacent to the surface to localize the insect in position.

Specific design for traps which target cockroaches are described in detail. The nematode supply, as described above, is placed into a suitably designed enclosure to provide the correct conditions for attraction and harboring of the roach population and the correct relative humidity. Because of the foregoing two requirements, the trap must be an enclosure, except, of course, for providing openings so that the roaches can enter. The design must provide an adequate space adjacent to the rough surface on which the nematodes will nictate to provide comfortable harborage for the roaches. In addition, provision must be made for maintaining the correct relative humidity at approximately 95% or greater at the surface of the gel.

Several designs may be employed. In a very simple configuration, shown in FIG. 1, a rolled piece of cardboard 101 is used to support the gel containing the nematodes, and the rolled cardboard is placed in a glass tube 102 open at each end. The relative humidity in the tube is maintained by the inherent moisture in the gel after the holes shown at the top of the tube 103 have been used for charging the cardboard support with the gel and supplying adequate moisture in the form of liquid water. These apertures are then sealed as shown 104 and the only remaining openings are at the ends of the tubes which permit the entry of the roach. This design can be maintained in an environment for 7-10 days after being charged with infective juveniles.

Figure 2:
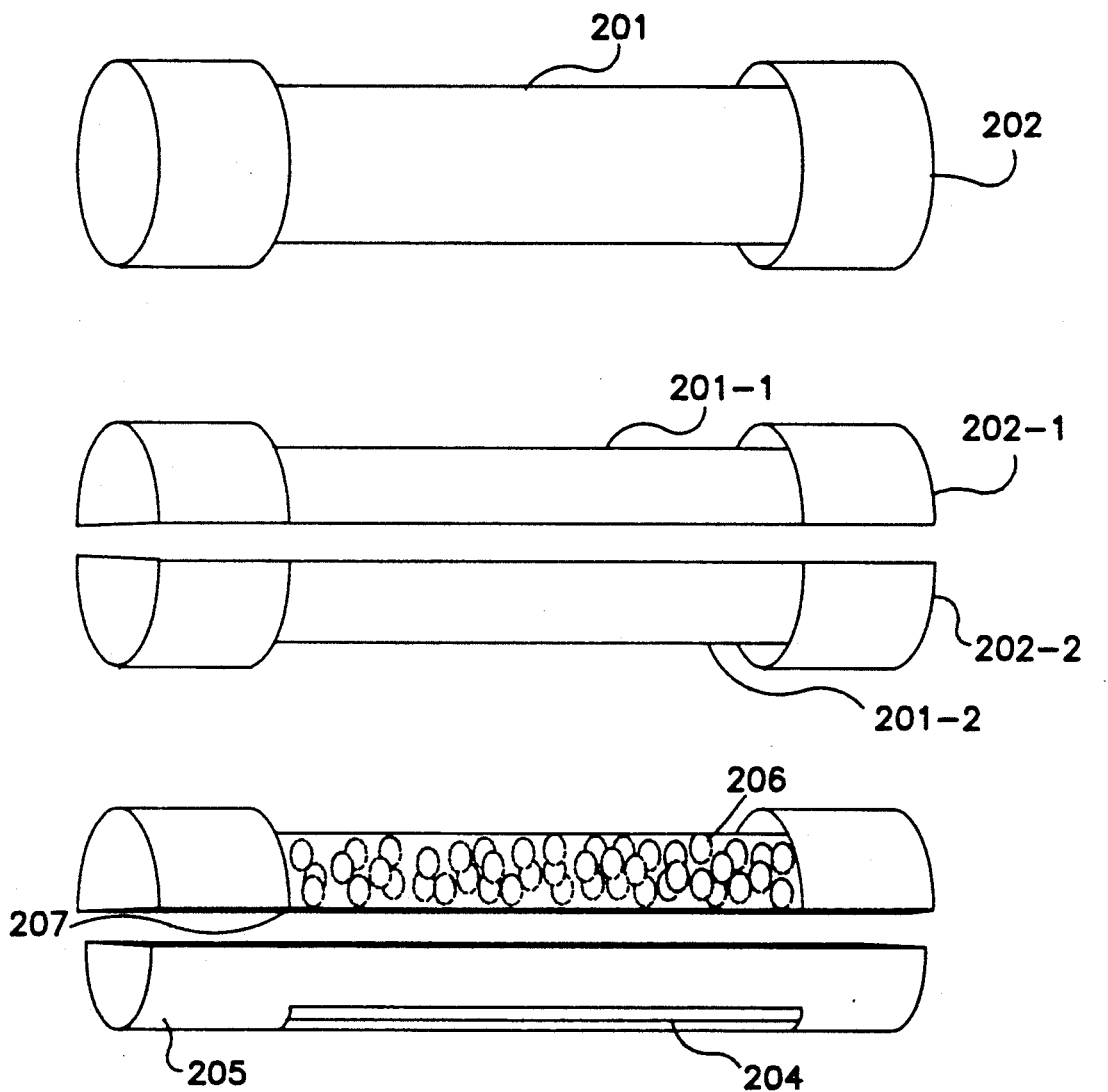
FIG. 2 shows an embodiment of the apparatus of the invention utilizing a polyvinyl chloride pipe as an enclosure and a hydrogel covered with sponge as a means for providing nematodes.

A preferred design, however, is shown in FIG. 2, which employs a polyvinyl chloride pipe with end caps as the housing. The PVC pipe 201 is cut in half lengthwise and the end caps 202 are removed. The bottom half of the pipe 201-2 is supplied with a sponge 204 into which the nematode-containing gel has been impregnated up to within a millimeter or so of the surface. The sponge containing the nematodes, when placed in the tube, does not occupy the entire surface area of the bottom half of the tube; space is left 205 so that the roaches which will enter from either end of the bottom half, as shown, have space in which to harbor. In this design, the relative humidity is maintained at the required 95% or greater level by molecular water supplied from either liquid water or water contained in a polyacrylamide bead preparation 206 separated from the lower half of the pipe by a membrane 207 which passes water only at a molecular level. Such membranes are commercially available under the trademark Tyvek ®. Other such membranes include spinbound polyolefin and forms of silicone rubber membranes. The membranes are preferably hydrophobic so that only molecular water is passed.

When the trap shown in FIG. 2 is assembled, the end caps remain 202-1 on the top half of the tube to seal in the water supply, but remain removed from the bottom half to permit entry of the roaches. The two halves of the tube are sealed together using, for example, duct tape.

Figure 3:
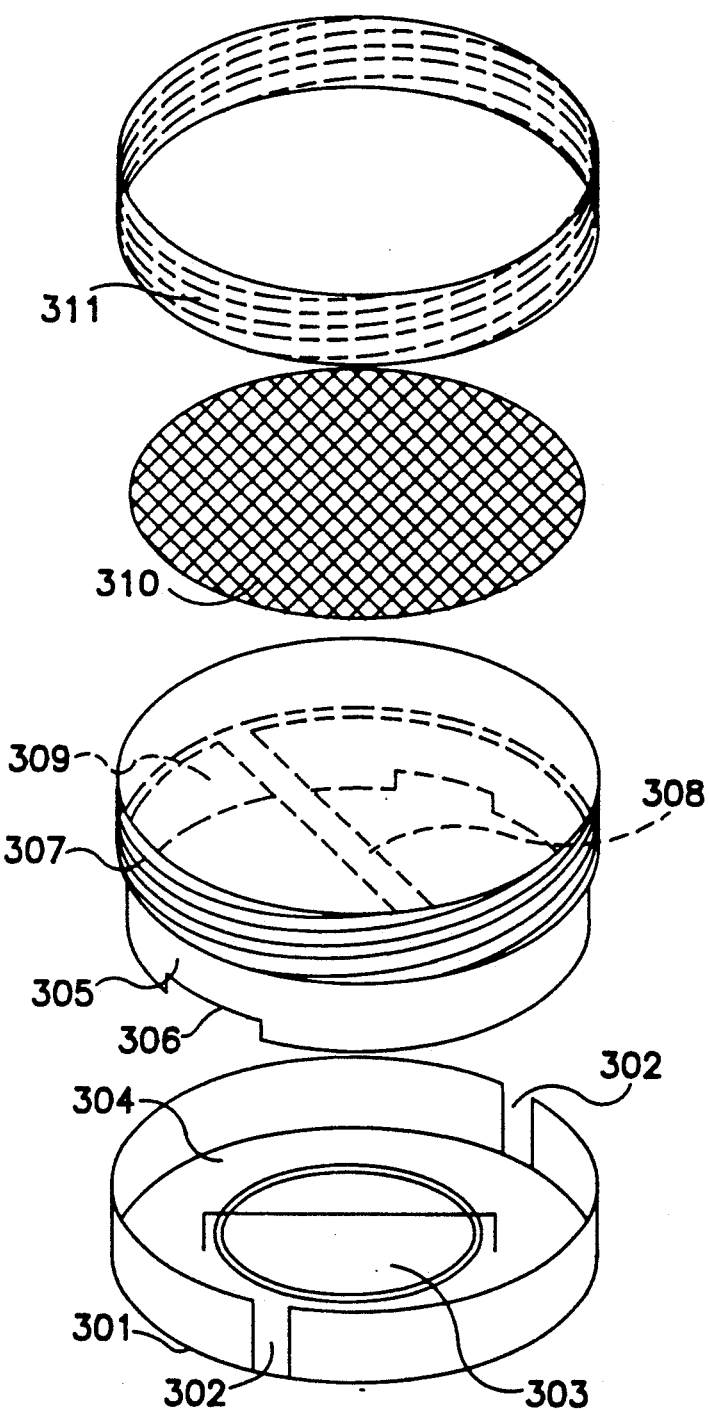
FIG. 3 shows an apparatus of the invention which provides a planar enclosure with controllable entrance points.

A preferred design of the trap is shown in FIG. 3. This configuration can, for example, have the approximate dimensions of a Petri dish. As shown in the figure, a planar bottom 301 contains openings 302 which will be used as entry ports. At the center of the surface 304 is a high surface area reticulated foam which is partially impregnated with a nematode suspension, shown at 303. As described above, the gel containing the IJ suspension leaves a 1-5 mm region at the top of the foam as a high surface area dried surface. The foam support 303 leaves sufficient perimeter 304 to provide suitable harborage for the roaches.

The base is provided with a sleeve 305 that has slots 306 which can be matched with the openings 302 to provide adjustable entry ports. The sleeve also contains a threaded portion 307 and a support bar 308 and flange 309 which will support the hydrophobic membrane 310 when the apparatus is assembled. Finally, a screw cap lid 311 is provided to fit the threads 307. When the apparatus is assembled, the sleeve 305 is placed over the base 301 and the membrane 310 on its supports in the sleeve. Water in liquid form, or preferably gelled into polyacrylamide, is then placed on the membrane and the screw cap 311 attached. The entry port size is adjusted by the matching of the slots 302 with those from the sleeve 306.

When assembled, the trap of FIG. 3 maintains a relative humidity in the vicinity of the gel of greater than 95%, and provides adequate harborage for the roaches. The nictation behavior caused by the surface area of the foam is sufficient that the IJs can infect the roaches and effect killing within 24 hours. Because, also, of the high surface area of the reticulated foam, the IJs do not appreciably escape from the pad in which they are contained.

In order to assure harborage, the trap should provide a path of approximately 1 cm of surface adjacent of the nictation-encouraging surface. Thus, in the design of FIG. 3, the gel-containing foam occupies only a fraction of the area. The gel-containing foam may be a disc of smaller diameter than the dish leaving the perimeter as harborage. Also the gel-containing foam may be provided in a complex pattern, leaving a "maze" of high surface area to harbor the insects.

The following examples are intended to illustrate, but not to limit, the invention.

EXAMPLE 1

EFFECTS OF RETICULATED SURFACE ON NICTATION

The roach trap to be tested is placed in an enclosed plastic box of the dimensions used commercially as sweater boxes. The trap is placed on one side of the box; at the other is placed an alternate attractant. In these experiments, a food source is used as the alternate attractant. Exactly 50 roaches are placed in the center of the box and the lid replaced. After a predetermined time of exposure, the roaches are removed from the box and the percent mortality determined after sufficient time for the toxins produced by the IJ-harbored symbionts to take effect.

In a first experiment, the trap similar to that shown in FIG. 3 was used. A standard petri dish plated with agar containing about $10^6$ IJs is used, and coated with a layer of polyurethane foam. The agar does not quite reach the outer circumference of the dish. The agar containing the IJs but without the foam was used alone in controls. Roaches were allowed to remain in the box for 30 seconds, 3 minutes or 10 minutes before removal.

The roaches were then observed for mortality. The sponge-treated agar-supplied traps provided 100% mortality after 24 hours when the roaches had been exposed for 10 minutes; 40% mortality was obtained after 24 hours when the roaches had been exposed for only 30 seconds; 85% mortality when exposed for 3 minutes. Use of agar without sponge produced only 55% mortality for a 10 minutes exposure after 24 hours; after 48 hours following the 10 minute exposure, the mortality rate was 78%. These results show that the sponge surface aids in the nictation behavior of the IJs.

The importance of including a rough surface to effect nictation behavior was especially dramatic when young roaches were used as subjects. When first instars were used in a 10 minute exposure in the protocol of the preceding paragraph, 100% mortality was achieved after 24 hours when the sponge-surfaced agar was used; when untreated agar was substituted in the trap, the mortality of the roaches was only 10% after 24 hours and increased only to about 15% after 50 hours.

EXAMPLE 2

EFFECT OF ENCLOSURE ON MORTALITY

The roaches were placed in plastic box "arenas" containing either a covered or uncovered trap. The mortality as a function of days after removal from exposure to these traps was determined. The covered trap ultimately effected approximately 70%, while the uncovered trap effected only about 35%.

We claim:

1. An apparatus for decreasing the population of insects in an environment, wherein said apparatus comprises:

an enclosure including a means by which an insect can enter said enclosure, and inside said enclosure acceptable to the insect, a source of live and active entomogenous infective juvenile nematodes;

a means to conduct said nematodes to a surface area acceptable to the insects in a manner which effects nictation behavior in said nematodes at the surface; and a means to maintain the relative humidity (RH) in the enclosure at 95% RH or greater;

said means to conduct said nematodes to said surface area being a hydrogel containing entomogenous infective juveniles maintained in a volume below an upper surface, said surface being a reticulated porous matrix.

2. The apparatus of claim 1 wherein said means to maintain RH introduces water in molecular form into the enclosure.

3. The apparatus of claim 1 wherein said means to conduct said nematodes to said surface area is a fiber pad containing entomogenous infective juveniles maintained in a volume below an upper surface.

4. The apparatus of claim 1 wherein said hydrogel comprises a polysaccharide.

5. The apparatus of claim 4 wherein said polysaccharide is agar, carrageenan, or tragacanth.

6. The apparatus of claim 1 wherein said reticulated porous matrix is polyurethane or polyether foam.

7. The apparatus of claim 1 wherein said means to conduct said nematodes to said surface area is a gel-nematode formulation surfaced with porous reticulated matrix.

8. The apparatus of claim 1 wherein said means to maintain relative humidity is a water source separated from the enclosure by a means for conducting molecular water.

9. The apparatus of claim 8 wherein said water source is a liquid water.

10. The apparatus of claim 8 wherein said water source is a hydrated gel.

11. The apparatus of claim 10 wherein the gel is polyacrylamide.

12. The apparatus of claim 1 wherein the insect is a cockroach and the enclosure includes means for diminishing light.

13. The apparatus of claim 12 wherein the surface area is a porous reticulated material adjacent to a smooth path.

14. The apparatus of claim 1 wherein the insect is a yellow jacket and the enclosure includes means to admit light.

15. The apparatus of claim 14 which further contains food, bait or other attractant.

16. The apparatus of claim 1 wherein the insect is a fly and the enclosure is elevated to permit entry by flight.

17. The apparatus of claim 16 which further contains food, bait, or other attractant.

18. A method to decrease the population of insects in an environment, which method comprises placing in said environment the apparatus of claim 1 in a position which permits insects to enter said enclosure for a time sufficient to decrease said population.

* * * * *